United States Patent [19]

Lee et al.

[11] Patent Number: 5,256,792
[45] Date of Patent: Oct. 26, 1993

[54] AMINE SALTS OF NITROAZOLES

[75] Inventors: Kien-yin Lee; Mary M. Stinecipher, both of Los Alamos, N. Mex.

[73] Assignee: The United States of America as represented by the United States Department of Energy, Washington, D.C.

[21] Appl. No.: 752,892

[22] Filed: Aug. 26, 1991

Related U.S. Application Data

[63] Continuation of Ser. No. 450,788, Dec. 14, 1989, abandoned.

[51] Int. Cl.$^5$ ............................................. C07D 249/12
[52] U.S. Cl. ............................................. 548/263.8
[58] Field of Search ..................................... 548/263.8

[56] References Cited

U.S. PATENT DOCUMENTS

| | | | |
|---|---|---|---|
| 3,054,800 | 9/1962 | Burchfield et al. | 260/299 |
| 3,111,524 | 11/1963 | Wiley et al. | 260/308 |
| 3,165,753 | 12/1965 | Smith et al. | 268/308 |
| 4,300,962 | 11/1981 | Stinecipher et al. | 149/47 |
| 4,552,598 | 11/1985 | Lee et al. | 149/92 |
| 4,733,610 | 3/1988 | Lee et al. II | 102/332 |

OTHER PUBLICATIONS

Kien-yin Lee et al. I, "3-Nitro-1,2,4-Triazol-5-One, A Less Sensitive Explosive," Los Alamos National Laboratory report LA-10302-MS (Feb. 1985).

Don T. Cromer et al. I, "Structure of the 1,3-Diaminoguanidinium Salt of 3-Nitro-1,2,4-Triazol-5-One, $CH_8N_5+C_2HN_4O_3$," Acta Cryst. 6 C44, 2206-2208 (1988).

Don T. Cromer et al. II, "The Structure of the Ethylenediammonium Salt of 3-Nitro-1,2,4-Triazol-5-One, $C_2H_4(NH_3)_2 \cdot 2C_2N_4O_3H^*$," Acta Cryst. C44, 1144-1147 (1988).

K.-Y Lee et al., "Binary Eutectics Formed Between Ammonium Nitrate and Amine Salts of 5-Nitrotetrazole I. Preparation and Initial Characterization," J. of Energetic Materials 1, 109-122 (1983).

Kien-Yin Lee et al. III, "Synthesis and Initial Characterization of Amine Salts of 3-Nitro-1,2,4-Triazol-5-one," Propellants, Explosives, Pyrotechnics 14, 241-244 (1989).

*Primary Examiner*—Patricia L. Morris
*Attorney, Agent, or Firm*—Richard J. Cordovano; Paul D. Gaetjens; William R. Moser

[57] ABSTRACT

Compositions of matter, a method of providing chemical energy by burning said compositions, and methods of making said compositions. These compositions are amine salts of nitroazoles.

1 Claim, 1 Drawing Sheet

NTO 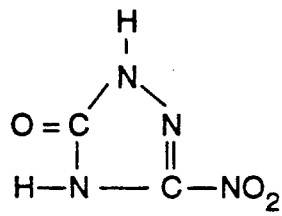
HYDRAZINE $H_2N-NH_2$
GUANIDINE 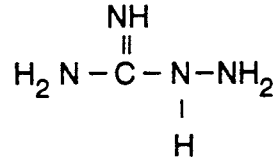
NT 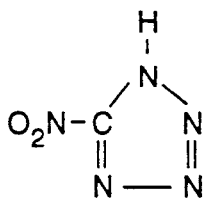
AG 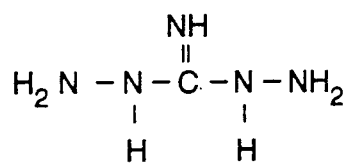
DNT 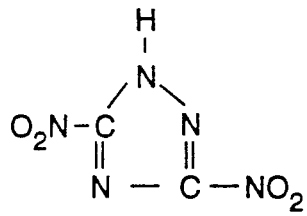
DAG 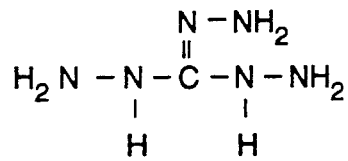
TAG
$$\begin{array}{c} N-NH_2 \\ \parallel \\ H_2N-N-C-N-NH_2 \\ | \quad\quad | \\ H \quad\quad H \end{array}$$

AMINE SALTS OF NITROAZOLES

This invention relates to the field of chemistry and, more particularly, to explosives and gun propellants. This invention is the result of a contract with the Department of Energy (Contract No. W-7405-ENG-36).

This is a continuation of application Ser. No. 07/450,788 filed Dec. 14, 1989, now abandoned.

BACKGROUND OF THE INVENTION

We are searching for new energetic materials to improve gun propellant formulations. The current goal of gun propellant development is to decrease the vulnerability of the propellant while retaining a high muzzle velocity. Theoretical calculations indicate that compounds containing a large amount of nitrogen produce gases of lower average molecular weight upon burning as compared to compounds with a large amount of carbon. Such low molecular weight gases contribute to higher impetus, since there are more moles of gas per unit weight of propellant. Compounds which are candidates for use as gun propellants will contain only carbon, nitrogen, oxygen, and hydrogen and will contain a high percentage of nitrogen. Also, candidate compounds will be thermally stable and moderately insensitive to impact. It is desirable to develop compounds with a lower sensitivity than RDX to mix with RDX, which is a well-known and widely used propellant ingredient, so that the mixture will have a reduced reaction to shock.

SUMMARY OF THE INVENTION

This invention is compositions of matter, a method of providing chemical energy by burning said compositions, and methods of making said compositions. A preferred use of said chemical energy is to propel projectiles. These compositions are amine salts of nitroazoles.

DESCRIPTION OF THE DRAWING

The drawing depicts the structural formulas of amines and nitroazoles which are components of the preferred chemical compounds. The nitroazole anion is formed by loss of one hydrogen ion and the amine cation is formed by gain of one hydrogen ion.

DETAILED DESCRIPTION OF THE INVENTION

Nitroazoles are five member heterocyclic molecules containing at least one nitrogen atom and at least one double bond and which have one or more nitro groups ($NO_2$) attached to the ring carbon atoms. The nitroazoles of this invention are selected from a group consisting of nitroimidazoles, nitropyrazoles, nitrotetrazole (NT) and nitrotriazoles such as 3,5-dinitro-1,2,4-triazole (DNT), and 3-nitro-1,2,4-triazol-5-one (NTO). The most suitable nitroazoles of this group for use in gun propellant formulations are believed to be the following compounds:
2,4-dinitroimidazole
4,5-dinitroimidazole
2,4,5-trinitroimidazole
3,5-dinitropyrazole
4-nitro-1,2,3-triazole
3-nitro-1,2,4-triazole
3,5-dinitro-1,2,4-triazole (DNT)
3-nitro,1,2,4-triazol-5-one (NTO) and
5-nitrotetrazole (NT).

Amines are organic compounds which may be considered derivatives of ammonia in which one or more hydrogen atoms have been replaced by hydrocarbon or nitrogen groups. The group of amines which may be used in this invention includes guanidine:
methylamine
methyl hydrazine
ethanolamine
1,2,3-triaminopropane
aziridine
diethylenetriamine
1,4-diaminobutane
pentaerythrityltetramine
biguanidine
biguanide
3,4,5-triamino-1,2,4-triazole
aminoguanidine (AG)
diaminoguanidine (DAG)
triaminoguanidine (TAG) and
hydrazine (H).

The inventive compounds which are preferred in that we believe they show the most promise for use as propellants are certain hydrazinium, guanidinium, aminoguanidinium, diaminoguanidinium, and triaminoguanidinium salts of 3-nitro-1,2,4-triazol-5-one (NTO), 5-nitrotetrazole (NT), and 3,5-dinitro-1,2,4-triazole (DNT). The compounds are:

hydrazinium 3-nitro-1,2,4-triazol-5-one (HNTO)
aminoguanidinium 3-nitro-1,2,4-triazol-5-one (AGNTO)
diaminoguanidinium 3-nitro-1,2,4-triazol-5-one (DAGNTO)
triaminoguanidinium 3-nitro-1,2,4-triazol-5-one (TAGNTO)
diaminoguanidinium 3,5-dintro-1,2,4-triazole (DAGDNT)
triaminoguanidinium 3,5-dintro-1,2,4-triazole (TAGDNT)
triaminoguanidinium 5-nitrotetrazole (TAGNT)
guanidinium 3-nitro-1,2,4-triazol-5-one (GNTO)

The choice of nitroazoles and amines for the development of improved propellants was made because they have sufficient acidity and basicity to form stable salts and contain relatively large amounts of nitrogen and oxygen. An amine cation has a high percentage of nitrogen and the nitroazole also provides nitrogen. Further, the nitroazole provides oxygen for burning of the fuel of the cation. In addition, because the oxidizer and fuel are chemically linked, the reactions in the flame zone and the detonation zone are not slowed by the necessity for the reactants to diffuse together.

Amine salts of nitroazoles may be synthesized by mixing a free amine base with a free nitroazole acid in solution and evaporating the solvent to obtain the salt in solid form. Any compatible solvent may be used, but water is the most convenient. The salt may be purified by redissolving in hot water or in a mixture of hot water and an alcohol and then recrystallizing by cooling the solution. The free amine base may be obtained by passing a water solution of a stable amine salt through an anion exchange resin to release the free amine base. Certain nitroazole are free acids. In other cases, the free nitroazole acid may be obtained by passing a water solution of a nitroazole salt through a cation exchange resin to release the free nitroazole acid. Also, the synthesis may be accomplished by a metathetical reaction, that is, a reaction between two salts in solution in which anions are exchanged. In addition, the synthesis may be accomplished by mixing an amine carbonate or bicarbonate with a solvent and then adding a free nitroazole acid to the solution.

Following are examples of synthesis of the preferred inventive compounds. The purity of the compounds synthesized was verified by elemental analysis and $^{13}$Carbon NMR spectroscopy. Table I lists the $^{13}$C NMR chemical shifts of the preferred compounds. The elemental quantities determined by analysis were in excellent agreement with theoretical values. $^{13}$C NMR spectra of the salts were recorded using a JEOL FX 90Q spectrometer operating at 90 MHz at room temperature. All samples were dissolved in deuterated dimethyl sulfoxide (DMSO-$d_6$). Values in Table I are in parts per million. There is a shoulder to the right of the AGNTO $C_1$ peak. $C_1$ is the guanidinium homolog carbon. The GNTO $C_1$ carbon has an NH group. $C_2$ is the carbon to which an $NO_2$ group is attached. $C_3$ is the carbon of a carbonyl group.

TABLE I

| Compound | Formula | $C_1$ | $C_2$ | $C_3$ |
|---|---|---|---|---|
| HNTO | $C_2H_6N_6O_3$ | — | 159.4 | 164.86 |
| GNTO | $C_3H_7N_7O_3$ | 158.6 | 159.12 | 164.86 |
| AGNTO | $C_3H_8N_8O_3$ | 159.33 | — | 164.86 |
| DAGNTO | $C_3H_9N_9O_3$ | 160.09 | 159.3 | 164.96 |
| TAGNTO | $C_3H_{10}N_{10}O_3$ | 159.2 | 160.0 | 165.0 |
| TAGNT | $C_2H_9N_{11}O_2$ | 159.1 | 169.0 | — |
| DAGDNT | $C_3H_8N_{10}O_3$ | 159.8 | 163.0 | — |
| TAGDNT | $C_3H_8N_{11}O_4$ | 159.1 | 163.0 | — |

$^{13}$CNMR CHEMICAL SHIFTS

EXAMPLE 1

Triaminoguanidinium Salt of NT (TAGNT)

An aqueous solution of triaminoguanidinium nitrate (1.67 g, 10 mmol) was passed through a column of Amberlite IRA-400 (OH$^-$ form) to release the free triaminoguanidine base (a column of Dowex 1-X8 may also be used), which was kept under an inert gas atmosphere. An aqueous solution of the ammonium salt of NT (1.32 g, 10 mmol) was passed through a cation exchanger, Dowex 50W-X8, to release the free nitrotetrazole acid. The acid and base thus obtained were combined to yield the salt. The water was removed and the solid residue recrystallized from ethanol/water and dried in a vacuum desiccator.

EXAMPLE 2

Hydrazinium Salt of NTO (HNTO)

A stoichiometric amount of hydrazine hydrate (0.75 ml, 15 mmol) was added slowly to a stirred aqueous solution of NTO (1.95 gm, 15 mmol). The resulting mixture was dried in a rotary evaporator. The yellowish residue obtained from the drying step was recrystallized from a water and ethanol mixture to obtain relatively pure HNTO.

EXAMPLE 3

Aminoguanidinium Salt of NTO (AGNTO)

An equal molar quantity of aminoguanidine bicarbonate (0.68 gm, 5 mmol) was added slowly to a stirred hot aqueous solution of NTO (0.65 gm, 5 mmol). The mixture was then evaporated to dryness in a hood at ambient temperature.

EXAMPLE 4

Diaminoguanidinium Salt of NTO (DAGNTO)

A solution of diaminoguanidine hydrochloride in water (1.33 gm, 10 mmol) was passed through a column of Amberlite IRA-400 (OH$^-$ form) to release the free diaminoguanidinium (DAG) base (a column of Dowex 1-X8 may also be used). Because the free DAG base is not stable in solution, it was immediately mixed with equal moles of NTO (1.30 gm, 10 mmol). The resulting mixture was evaporated to dryness in a hood at ambient temperature. DAGNTO crystallized out as pale, straw-colored crystals.

EXAMPLE 5

Triaminoguanidinium Salt of NTO (TAGNTO)

An aqueous solution of triaminoguanidinium nitrate (1.67 gm, 10 mmol) was passed through a column of Amberlite IRA-400 (OH$^-$ form) to release the free TAG base (a column of Dowex 1-X8 may also be used), which was then mixed with equal moles of NTO (1.30 mg, 10 mmol). Pure TAGNTO was obtained by recrystallization from a water and alcohol mixture.

EXAMPLE 6

Diaminoguanidinium Salt of DNT (DAGDNT)

Solutions of 1.89 g (15 mmol) diaminoguanidinium hydrochloride in 10 ml water and 2.64 g (15 mmol) ammonium salt of 3,5-dinitro-1,2,4-triazole in 10 ml water were mixed. On cooling and reducing the amount of water to 5 ml, light yellow crystals precipitated. The crystals were filtered, washed with cold water, and recrystallized from hot water. The product was dried in a vacuum desiccator. The yield was 3.26 g of DAGDNT (88% yield).

EXAMPLE 7

Triaminoguanidinium Salt of DNT (TAGDNT)

An aqueous solution of triaminoguanidinium nitrate (1.05 g, 6.3 mmol) in 40 ml of water was added to a solution of the ammonium salt of DNT (1.1 g, 6.3 mmol) in 10 ml of water. The water was evaporated until crystals formed. The crystals were filtered, washed with cold water, recrystallized from hot water, and dried in a vacuum desiccator.

EXAMPLE 8

Guanidinium Salt of NTO (GNTO)

To a stirred aqueous solution of guanidine carbonate, equal moles of NTO were added gradually until all dissolved. The mixture was evaporated to dryness at ambient temperature. After recrystallization from water, a hydrated GNTO crystal was obtained. The water was removed by drying in a vacuum oven at 90° C.

Table II shows certain properties of the preferred compounds. RDX is a common propellant ingredient which is included in this table and others for purposes of comparison. The density of DAGNTO was determined by x-ray crystallography. Other densities, except that of RDX, are estimated.

TABLE II

PROPERTIES

| Compound | Molecular Weight | Density (g/cm$^3$) | Melting Point (°C.) |
|---|---|---|---|
| RDX | 222 | 1.81 | 205 |
| HNTO | 162 | 1.65 | 170 |
| GNTO | 189 | 1.60 | 210 |
| AGNTO | 204 | 1.64 | 194 |
| DAGNTO | 219 | 1.67 | 208 |
| TAGNTO | 234 | 1.62 | 180 |
| TAGNT | 219 | 1.58 | 94 |
| DAGDNT | 248 | 1.68 | 145 |
| TAGDNT | 263 | 1.61 | 165 |

The new compounds were subjected to small-scale sensitivity tests in accordance with standard procedures. The results are reported in Table III. The compounds are listed in order of increasing percentage of nitrogen within each family. As the nitrogen content of the guanidinium homolog salts increases, it appears that thermal stability decreases and impact sensitivity increases. However, all the compounds are significantly less sensitive to impact and spark than RDX. GNTO and AGNTO did not show a response to the impact test.

TABLE III

EXPLOSIVE PROPERTIES

| Compound | Nitrogen (%) | Diff. Thermal Analysis Exotherm (°C.) | Drop-Weight Impact Height Type 12 (cm) | Spark Test 3-Mil foil (J) |
|---|---|---|---|---|
| RDX | 37.84 | 205 | 22 | 0.2 |
| HNTO | 51.84 | 170 | 92 | >1.0 |
| GNTO | 51.84 | 260 | no go | >1.0 |
| AGNTO | 54.89 | 200 | no go | >1.0 |
| DAGNTO | 57.52 | 190 | 252 | >1.0 |
| TAGNTO | 59.81 | 170 | 103 | >1.0 |
| TAGNT | 70.30 | 156 | <15 | >0.75 |
| DAGDNT | 56.44 | 240 | 34 | >1.0 |
| TAGDNT | 58.54 | 236 | 31 | >1.0 |

To estimate the performance of these new compounds as gun propellants, we calculated the impetus and flame temperature of each salt using the Blake thermodynamic gun propellant performance code furnished by the Ballistic Research Laboratory of the U.S. Army. The results are presented in Table IV. Heat of formation of a compound is required in order to complete performance calculations. The heat of formation of a new compound can be estimated from heats of formation of similar known compounds. But, for best results, the heat of formation of a compound is determined from the measured heat of combustion. The heat of formation at standard temperature and pressure (298 K, 1 atmosphere) of each salt was calculated from the heat of combustion measured by burning the compound in a Parr combustion bomb under 30 atm oxygen pressure.

High nitrogen compounds often leave residues after burning because their burning temperatures are low. When necessary, a standard (such as benzoic acid) was mixed with the sample to obtain a complete burn. The heat of formation of the sample was then calculated after subtracting the heat of combustion of benzoic acid from the measured gross heat of combustion. To correct the heat of combustion for nitric acid formation, bomb washings were titrated with standard sodium carbonate (0.0453M) solution in all the runs. Table IV includes chemical formulas and heats of formation, which are the data input for the Blake calculations. The loading density used in the calculations was 0.2 g/cm$^3$. The heat of formation of TAGNT was estimated.

TABLE IV

BLAKE CALCULATIONS

| Compound | Formula | Heat of Formation (kcal/mole) | Impetus (J/g) | Flame Temperature (K) |
|---|---|---|---|---|
| RDX | $C_3H_6N_6O_6$ | 14.7 | 1386 | 4060 |
| HNTO | $C_2H_6N_6O_3$ | $-38 \pm 5$ | 799 | 1988 |
| GNTO | $C_3H_7N_7O_3$ | $-71 \pm 3$ | 531 | 1489 |
| AGNTO | $C_3H_8N_8O_3$ | $-42.5 \pm 2.3$ | 630 | 1644 |
| DAGNTO | $C_3H_9N_9O_3$ | $-21 \pm 2$ | 708 | 1768 |
| TAGNTO | $C_3H_{10}N_{10}O_3$ | $14 \pm 4$ | 836 | 1980 |
| TAGNT | $C_2H_9N_{11}O_2$ | 94 (calc) | 1113 | 2531 |
| DAGDNT | $C_3H_8N_{10}O_3$ | $-34.5 \pm 4.7$ | 1069 | 2675 |
| TAGDNT | $C_3H_8N_{11}O_4$ | $59.8 \pm 0.2$ | 1242 | 2797 |

What is claimed is:

1. Compositions which are salts of 3-nitro-1,2,4-triazol-5-one, where a salt is formed from 3-nitro-1,2,4-triazol-5-one and a compound selected from a group consisting of hydrazine, guanidine, aminoguanidine, diaminoguanidine, and triaminoguanidine.

* * * * *